United States Patent [19]

DeBernardis et al.

[11] Patent Number: 5,389,638

[45] Date of Patent: Feb. 14, 1995

[54] TETRAHYDROISOQUINOLINES AS ALPHA-2 ANTAGONISTS AND BIOGENIC AMINE UPTAKE INHIBITORS

[75] Inventors: John F. DeBernardis, Lindenhurst; Daniel J. Kerkman, Lake Villa, both of Ill.; Robert E. Zelle, Stow, Mass.; William McClellan, Waukegan, Ill.

[73] Assignee: Abbott Laboratories, Abbott Park, Ill.

[21] Appl. No.: 119,789

[22] Filed: Sep. 10, 1993

[51] Int. Cl.⁶ .................. N61K 31/47; C07D 217/18; C07D 401/06

[52] U.S. Cl. ........................... 514/29.1; 514/307; 514/309; 546/90; 546/146; 546/150; 546/141

[58] Field of Search ............... 546/141, 146, 147, 148, 546/149, 90, 150; 514/307, 309, 291

[56] References Cited

U.S. PATENT DOCUMENTS

| | | | |
|---|---|---|---|
| 3,676,444 | 7/1972 | Archer et al. | 260/287 |
| 3,682,926 | 8/1972 | Sydney et al. | 260/287 |
| 3,728,352 | 4/1973 | Archer et al. | 260/287 R |
| 3,985,881 | 10/1976 | Mehrhof et al. | 424/258 |
| 3,994,891 | 11/1976 | Hughes et al. | 260/247.5 |
| 4,232,160 | 11/1980 | Schut et al. | 546/146 |
| 4,362,875 | 12/1982 | Seubert | 546/146 |
| 5,041,451 | 8/1991 | Colle et al. | 514/301 |
| 5,118,690 | 6/1992 | Minchin et al. | 514/314 |

FOREIGN PATENT DOCUMENTS

| | | |
|---|---|---|
| 8930293 | 2/1989 | Australia . |
| 0232989 | 8/1987 | European Pat. Off. . |
| 0330360 | 8/1989 | European Pat. Off. . |
| 0370732 | 5/1990 | European Pat. Off. . |
| 0409489 | 1/1991 | European Pat. Off. . |
| 9313073 | 7/1993 | WIPO . |

OTHER PUBLICATIONS

Hromatka et al, Monatsh. Chem. vol. 97, No. (1), pp. 19-32, 1966.

*Primary Examiner*—C. Warren Ivy
*Assistant Examiner*—Zinna N. Davis
*Attorney, Agent, or Firm*—Jerry F. Janssen

[57] ABSTRACT

The present invention provides a tetrahydroisoquinoline compound of the formula

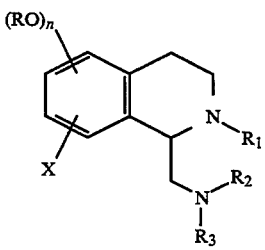

or a pharmaceutically acceptable salt thereof which is an antagonist for alpha-2 adrenoreceptors and/or which inhibits biogenic amine uptake.

10 Claims, No Drawings

TETRAHYDROISOQUINOLINES AS ALPHA-2 ANTAGONISTS AND BIOGENIC AMINE UPTAKE INHIBITORS

TECHNICAL FIELD

The present invention relates to novel organic compounds and compositions which are alpha-2 adrenoreceptor antagonists and/or biogenic amine uptake inhibitors, pharmaceutical compositions comprising the compounds, and a method for treating diseases of the central nervous system including depression, agression, obsessive compulsive disorders, panic attacks, memory disturbances, anxiety, hypochondriasis, and aspects of Alzheimer's disease, diseases of the vascular system including hypertension, glaucoma and migraine, metabolic disorders such as diabetes or feeding disorders, and alcoholism.

BACKGROUND OF THE INVENTION

The adrenergic nervous system plays a major role in the innervation of heart, blood vessel and smooth muscle tissue. Compounds capable of interacting with receptor sites within the adrenergic nervous system can initiate a variety of physiological responses, including vasoconstriction, vasodilation, and increased or decreased heart rate (chronotropic), contactility (inotropic) and metabolic activity. The adrenergic receptor system is complex, having a number of receptor types and sub-types, each involved in particular functions. In the past, various adrenergic compounds have been employed to affect these and other physiological responses. However, many adrenergic compounds do not possess significant selectivity for particular adrenergic receptors to produce the desirable interactions with adrenergic receptor sites without also causing undesirable side-effects. That is, these adrenergic compounds do not demonstrate a high degree of specificity for differing receptors types within the adrenergic nervous system in order to obtain a desired physiological response separate from other possible, and perhaps less desirable, responses of the system.

SUMMARY OF THE INVENTION

The compounds of the present invention demonstrate the ability to selectively inhibit alpha-2 adrenergic receptors, i.e. are alpha-2 antagonists, which are mainly distributed on the membranes of central and peripheral adrenergic neurons and on the tissues innervated thereby. The compounds of this invention are also effective in inhibiting biogenic amine uptake. As used herein, the term "biogenic amine" refers to one or more of the compounds selected from the group consisting of norepinephrine, serotonin, dopamine and the like.

By inhibiting interaction with the alpha-adrenergic receptors in the peripheral nervous system, one can modulate the function of adrenergic neurons and hemodynamic equilibrium which is therapeutically useful in a multitude of cardiovascular indications, such as hypertension, congestive heart failure, and a variety of vascular spastic conditions. Furthermore, the alpha-adrenergic antagonists are useful in certain neurological and psychiatric disorders such as depression. Dual pharmacophores which are alpha-2 antagonists and also inhibit the uptake of biogenic amines have a beneficial synergistic effect in the treatment of depression with enhanced efficacy over each type of activity alone, the potential for faster onset of action and/or efficacy among non-responding patients while perhaps having a desirable side effect profile.

In accordance with the principal embodiment of the present invention, there are provided alpha-2 adrenoreceptor antagonists and/or biogenic amine uptake inhibiting compounds of the Formula I:

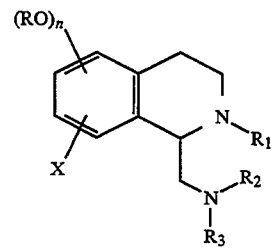

or a pharmaceutically acceptable salt thereof, where n is an integer having the value of of 0,1 or 2, and R is independently selected from the group consisting of methyl, ethyl, and, when n=2, methylenedioxy.

The group X is selected from hydrogen and fluorine, and $R_1$ is selected from the group consisting of alkyl of one to six carbon atoms, alkanoyl, of from two to six carbon atoms, aminosulfonyl, alkoxycarbonyl of from two to eight carbon atoms; and aminocarbonyl.

The group $R_2$ is selected from methyl and ethyl, and $R_3$ is arylalkyl where the aryl portion is unsubstituted or is substituted by one or more groups selected from the group consisting of alkyl of one to six carbon atoms, haloalkyl of one to six carbon atoms, alkoxy of one to six carbon atoms, thioalkoxy of one to six carbon atoms, amino, alkylamino of one to six carbon atoms, dialkylamino in which the alkyl groups are independently of one to six carbon atom, hydroxy, halo, mercapto, nitro, carboxaldehyde, carboxy, carboalkoxy of two to eight carbon atoms, and carboxamido. Alternatively, $R_2$ and $R_3$ taken together with the nitrogen to which they are attached form a 5- or 6-membered ring optionally substituted by phenyl, optionally substituted by one or more groups selected from alkyl of one to six carbon atoms, halo, hydroxy, alkoxy of one to six carbon atoms, amino, and thioalkyloxy of one to six carbon atoms.

The pharmaceutically acceptable salts and individual stereoisomers of compounds of structural formula I above, as well as mixtures thereof, are also contemplated as falling within the scope of the present invention.

In another aspect, the present invention also relates to a method for antagonizing alpha-2 adrenoreceptor activity and/or inhibiting biogenic amine uptake in a mammal in need of such treatment, comprising administering to the mammal a therapeutically effective amount of a compound of claim 1.

The invention further relates to alpha-2 adrenoreceptor antagonist and/or biogenic amine uptake inhibiting compositions comprising a pharmaceutical carder and a therapeutically effective amount of a compound of claim 1.

In yet another aspect of the present invention, there is provided a method of treating diseases of the central nervous system including depression, agression, obsessive compulsive disorders, panic attacks, hypochondriasis, memory disturbances, and anxiety, diseases of the vascular system including hypertension, glaucoma and migraine, metabolic disorders such as diabetes or feeding disorders, and alcoholism by administering to a host mammal in need of such treatment a therapeutically effective amount of a compound of claim 1.

DETAILED DESCRIPTION OF THE INVENTION

In one preferred embodiment of the present invention, compounds are represented by Formula II:

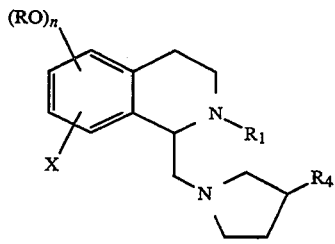

where X, R, $R_1$, and n are as defined above and and $R_4$ is phenyl, optionally substituted with one or more groups selected from alkyl of one to six carbon atoms, halo, hydroxy, alkoxy of one to six carbon atoms, amino, and thioalkyloxy of one to six carbon atoms.

In another preferred embodiment, compounds are represented by Formula III:

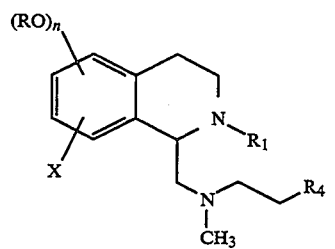

where X, R, $R_1$, $R_4$ and n are as defined above.

In a particularly referred embodiment, n is 2, the —OR radicals are in positions 5- and 6- or 6- and 7- positions of the tetrahydroisoquinoline moiety.

Examples of compounds falling within the scope of the present invention include, but are not limited to, the following:

6-methoxy-2-methyl-1-(3-phenylpyrrolidino)methyl-1,2,3,4-tetrahydroisoquinoline;
6-methoxy-2-methyl-1-(((N-methyl-N-(2-phenylethyl)amino)methyl)-1,2,3,4-tetrahydroisoquinoline;
5-methoxy-2-methyl-1-(3-phenylpyrrolidino)methyl-1,2,3,4-tetrahydroisoquinoline;
5,6-methylenedioxy-2-methyl-1-((N-methyl-N-(2-phenylethyl)amino)methyl)-1,2,3,4-tetrahydroisoquinoline;
5,6-methylenedioxy-2-methyl-1-(N-(3-phenylpyrrolidino)methyl-1,2,3,4-tetrahydroisoquinoline;
6,7-methylenedioxy-2-methyl-1-(3-phenylpyrrolidino)-methyl-1,2,3,4-tetrahydroisoquinoline;
6,7-methylenedioxy-2-methyl-1-((N-methyl-N-(2-phenylethyl)amino)methyl)-1,2,3,4-tetrahydroisoquinoline;
5,6-methylenedioxy-2-methyl-1(R)-(3'(R)-phenylpyrrolidino)methyl-1,2,3,4-tetrahydroisoquinoline;
5,6-methylenedioxy-2-methyl-1(R)-(3'(S)-phenylpyrrolidino)methyl-1,2,3,4-tetrahydroisoquinoline;
5,6-methylenedioxy-2-methyl-1-(S)-(3'R)-phenylpyrrolidino)methyl-1,2,3,4-tetrahydroisoquinoline;
5,6-methylenedioxy-2-methyl-1(S)-(3'(S)-phenylpyrrolidino)methyl-1,2,3,4-tetrahydroisoquinoline;
5,6-methylenedioxy-2-methyl-1(R)-((N-methyl-N-(2phenylethyl)amino)methyl)-1,2,3,4-tetrahydroisoquinoline; and
5,6-methylenedioxy-2-methyl-1(S)-((N-methyl-N-(2-phenylethyl)amino)methyl)-1,2,3,4-tetrahydroisoquinoline or a pharmaceutically acceptable salt of any of the foregoing.

As used throughout this specification and the appended claims, the following terms have the meanings ascribed to them:

The term "lower alkyl" as used herein refers to straight or branched chain saturated hydrocarbon radicals having from one to six carbon atoms. Representative examples of lower alkyl groups include methyl, ethyl, n-propyl, iso-propyl, n-butyl, sec-butyl, iso-butyl, tert-butyl, and the like.

The term "lower alkoxy" as used herein refers to a lower alkyl group, as defined herein, which is bonded to the parent molecular moiety through an oxygen atom. Representative examples of lower alkoxy groups include methoxy, ethoxy, tert-butoxy, and the like.

The term "alkanoyl" as used herein refers to a hydrogen or lower alkyl group, as defined herein, which is bonded to the parent molecular moiety through a carbonyl group. Representative examples of alkanoyl groups include, but are not limited to, formyl, acetyl, propionyl, isobutyryl and the like.

The term "alkylsulfonyl" or "arylsulfonyl" as used herein refer to a lower alkyl group, as defined herein, or an aryl group, as defined herein, which is bonded to the parent molecular moiety through a sulfonyl, $>SO_2$, group. Representative examples of alkylsulfonyl and aryl sulfonyl groups include, but are not limited to, methanesulfonyl, ethanesulfonyl, benzenesulfonyl and the like.

The term "aminocarbonyl" as used herein refers to an amino group which may be unsubstituted, mono-substituted or di-substituted, which is bonded to the parent molecular moiety through a carbonyl group. Representative examples of aminocarbonyl include, but are not limited to, aminocarbonyl, dimethylaminocarbonyl, diethylaminocarbonyl and the like.

The term "aryl" as used herein refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide. In addition, substituted aryl groups include tetrafluorophenyl and pentafluorophenyl.

The term "arylalkyl" as used herein refers to an aryl group as previously defined, appended to a loweralkyl radical, for example, benzyl and the like.

The term "halo" or "halogen" as used herein means fluorine, iodine, bromine, or chlorine.

The term "methylenedioxy" as used herein refers to the group, —OCH$_2$O—, attached to adjacent carbon atoms on the parent molecular moiety to form a five-membered ring.

The term "substituted phenyl" as used herein refers to a phenyl ring with one, two, or three substituents independently selected from lower alkyl, halo, hydroxy, lower alkoxy, amino, and thioalkyloxy.

The term "pharmaceutically acceptable salts" refers to the pharmaceutically acceptable, relatively nontoxic, inorganic or organic acid addition salts of the compounds of the present invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitate, methanesulfonate, stearate, laurate, borate, benzoate, lactate, phosphate, tolsylate, citrate, maleate, fumarate, succinate, tartrate, napsylate, and the like. Those compounds having more than one basic site can be isolated as bis-salts, for example, dihydrochloride, bis-methanesulfonate, and the like.

The standard chirality descriptors "R" and "S" are used to indicate an isomerically pure center, "RS" to indicate a mixture, and "R/S" to indicate a single pure isomer of undetermined configuration. The assignment of "R" and "S" depends on the priority ranking of atoms or groups attached to the asymmetric center as determined by the Cahn-Ingold-Prelog Sequence Rule (International Union of Pure and Applied Chemistry, "Nomenclature of Organic Chemistry, Sections, A, B, C, D, E, F, and H", Pergamon Press, Oxford, 1979; Cahn, R. S., Ingold, C. K., Prelog, V., *Angew. Chem., Int. Ed. Engl.* 1966, 5: 385; and Prelog, V., Helmchen, G., *Angew. Chem., Int. Ed. Engl.* 1982, 21: 567).

Biological Assay Methods

The compounds were assessed for alpha-adrenergic receptor activity by use of radioligand binding techniques as described previously (DeBernardis et al., *J. Med. Chem.*, 1985, 28: 1398). Affinity for the alpha-1 receptor was assessed using rat liver homogenates and the radioligand [$^3$H]-prazosin; whereas for the alpha-2 receptor, rat cerebral cortices and the radioligand [3H]-rauwolscine were utilized. Results obtained from the binding studies are shown in Table 1 for a representative sample of compounds disclosed herein, showing clearly the excellent affinity for the alpha-2 receptor, as well as the high degree of selectivity relative to the alpha-1 adrenoreceptor.

The primary method of evaluation of biogenic amine uptake activity has been the in vitro determination of the inhibition of radioactive amine uptake by synaptosome preparations of brain tissue. Basic procedures used are those described by Snyder and Coyle (Snyder, S. H. and J. T. Coyle, Regional Differences in $^3$H-Norepinephrine and $^3$H-Dopamine Uptake into Rat Brain Homogenates, *Journal of Pharmacology and Experimental Therapeutics* 1969, 165: 78–86) and Wong et al. (Wong, D. T., J-S. Horng and R. W. Fuller, Kinetics of Norepinephrine Accumulation into Synaptosomes of Rat Brain-Effects of Amphetamine and Chloroamphetamines, *Biochemical Pharmacology* 1973, 22:311–322). Briefly, male Sprague-Dawley rats were decapitated and regions of their brains dissected according to the procedures of Glowinski and Iversen (Glowinski, J. and L. L. Iversen, Regional Studies of Catecholamines in the Rat Brain—I: The Disposition of [$^3$H]-Norepinephrine, [$^3$H]-Dopamine and [$^3$H]-DOPA in Various Regions of the Brain, *Journal of Neurochemistry* 1966, 13: 655–669). Hypothalamus (norepinephrine-), cortex (serotonin) and striatum (dopamine-uptake) were homogenized in 10, 5, and 20 volumes, respectively, of 0.32M sucrose using a Teflon/glass Potter-Elvehjem tissue grinder. Samples were centrifuged at 1000×G for 10 minutes and the supernatants harvested and used in the assay. Aliquots of tissue (100 mL) were added to 750 mL of Kreb's solution (composition in mM; sodium chloride 118, potassium chloride 4.0, calcium chloride 1.13, potassium dihydrogen phosphate 1.12, magnesium sulfate 1.20, sodium bicarbonate 2.4, D-glucose 5.0, disodium ethylenediaminetetraacetic acid 1.5, ascorbic acid 1.0, and Pargyline, 12.5 mM, pH=7.4, aerated with 95% oxygen, 5% carbon dioxide), 50 mL of test compound diluted in 0.3 mM ascorbic acid, and 100 mL [$^3$H]-amine, final concentration approximately 100 nM. Tissues were incubated for 4 minutes at 37° C., followed by rapid vacuum filtration over Whatman GF/B filters and washed with 50 mM Tris-HCl (pH=7.4). Nonspecific uptake was estimated in duplicate samples incubated at 0 ° C. Data were analyzed as described previously (J. F. DeBernardis, D. J. Kerkman, D. L. Arendsen, S. A. Buckner, J. J. Kyncl, and A. A. Hancock, Conformationally Defined Adrenergic Agents. 5. Resolution, Absolute Configuration, and Pharmacological Characterization of the Enantiomers of 2-[5,6-Dihyroxy-1,2,3,4-tetrahydro-1-1-naphthyl]imidazoline: A Potent Agonist at a-Adrenoceptors, *Journal of Medicinal Chemistry* 1987, 30: 1011–1017).

TABLE 1

| EXAMPLE | RADIOLIGAND BINDING $K_i$ (nM) | | ALPHA-2 SELECTIVITY (nM) | BIOGENIC AMINE UPTAKE $IC_{50}$ (nM) | | |
|---|---|---|---|---|---|---|
| | α1 | α2 | $K_i$α1/$K_i$α2 | NE | 5-HT | DA |
| 1 | 120 | 6.2 | 19 | 4434 | 9185 | 28311 |
| 2 | 175 | 4.6 | 38 | 1236 | 7708 | 26472 |
| 3 | 306 | 6.0 | 51 | 621 | 4447 | 9402 |
| 4 | 621 | 2.6 | 238 | 885 | 2600 | 24729 |
| 5 | 180 | 4.3 | 42 | 249 | 2026 | 11402 |
| 6 | 72 | 11.4 | 6 | NT | NT | NT |
| 7 | 613 | 6.4 | 96 | 589 | 6268 | 49753 |
| 8 | 446 | 2.5 | 178 | 489 | 1106 | 9302 |
| 9 | 168 | 2.1 | 80 | 426 | 1579 | 9545 |
| 10 | 374 | 20.2 | 18.5 | 214 | 754 | 11658 |
| 11 | 157 | 32.5 | 4.8 | 116 | 1695 | 4951 |
| 12 | 1016 | 0.98 | 1037 | 1289 | 1406 | 25514 |
| 13 | 542 | 7.1 | 76 | 210 | 2891 | 10559 |
| Rauw* | 450 | 2.8 | | >100 | >100 | >100 |
| Fluoxetine | >1000 | >1000 | | 1307 | 300 | 15193 |

Rauw* is Rauwolscine

The compounds of the invention can be administered in any effective pharmaceutically acceptable form to warm blooded animals, e.g., in oral, parenteral or infusable dosage forms, or as a buccal or nasal spray. Suitable routes of administration include, for example, intramuscular, intravenous, intraperitoneal or subcutaneous administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or other sterile injectable medium, immediately before use.

Solid dosage forms for oral admistration include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides such inert diluents, compositions may also comprise adjuvants, such as wetting agents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the activity of the particular compound, the desired therapeutic effect, the route of administration, the desired duration of treatment, the severity of the condition being treated, the condition and prior medical history of the patient being treated and other factors. However, it is within the skill of the art to start doses of the compound at levels lower than required to achieve the desired therapeutic effect and to gradually increase the dosage until the desired effect is achieved.

Generally, dosage levels of about 0.1 to 1000 mg, more preferably about 1 to 150 mg and most preferably about 0.5 to 125 mg of active ingredient per kg of body weight per day are administered orally to a mammalian patient suffering from depression. If desired, the daily dose may be divided into multiple doses for administration, e.g., two to four separate doses per day.

Asymmetric centers exist in the compounds of the present invention. Unless otherwise specified, a chiral compound of the present invention contemplates the various stereoisomers and mixtures thereof. Starting compounds of particular stereochemistry are either commercially available or are made by the methods detailed below and resolved by techniques well-known in the organic chemical arts.

In general, the compounds of the present invention can be prepared as illustrated in Schemes 1-7. For illustration purposes, the case where X is hydrogen is shown.

In Scheme 1,3-methoxyphenylethylamine is reacted with formaldehyde to give an imine which cyclizes under acidic conditions to give tetrahydroisoquinoline 1. Treatment of 1 with Fremy's salt followed by quaternization with methyl iodide gives the dihydroisequinolinium salt 2. Treatment of 2 with potassium cyanide gives the 1-cyano compound 3. Reduction of the nitrile (for example, with aluminum hydride) give the 1-methylamino compound 4. Intermediate 4 can either be reacted with phenylsuccinic anhydride in the presence of an acid chloride to give the phenylsuccinimide 5. Reduction of 5 with a reagent such as lithium aluminum hydride give the pyrrolidino compound 6.

Alternatively intermediate 4 is reductively methylated using ethyl formate followed by borane reduction to give the methylaminomethyl compound 7. Treatment of 7 with an arylalkanoic acid such as phenyl acetic acid in the presence of a coupling reagent such as dicyclohexylcarbondiimide gives carboxamide 8. Reduction of 8, for example with borane, gives the corresponding phenylalkyl tertiary amine 9.

Scheme 2 illustrates the preparation of the 5-methoxy compound. The starting 5-hydroxyisoquinoline is reduced in acetic acid with a platinum catalyst to give the tetrahydro compound 10. Treatment of 10 with sodium acetate in acetic anhydride gives the N-acetyl compound 11. O-Alkylation with methyl iodide in the presence of potassium carbonate gives the O-methyl compound 12. Acid hydrolysis using for example, hydrogen chloride in methanol, gives the amine salt 13. This intermediate is then carded on by the reactions described in Scheme 1 for the preparation of compound 6 to give the pyrrolidino compound 18.

Scheme 3 describes the preparation of the 5,6-methylenedioxy compounds. 2,3-Dihydroxybenzaldehyde is treated with bromochloromethane in the presence of cesium carbonate in DMF to give the 5,6-methylenedioxy compound 19. Treatment of 19 with nitromethane gives the nitro styrene compound 20. Reduction of the styrene double bond (for example, with borohydride) gives the nitro ethyl compound 21. Catalytic hydrogenation of compound 21 in the presence of Raney nickel gives the aminoethyl compound 22. Acylation of 22 with ethyl chloroformate gives the ethyl carbamate 23. Treatment of 23 with glyoxylic acid under acidic conditions gives the tetrahydroisoquinoline compound 24. Intermediate 24 can be reacted with N-methyl-N-phenylethylamine to give compound 25. Lithium aluminum hydride reduction gives tertiary amine 26.

Alternatively intermediate 24 is reacted with 3-phenylpyrrolidine to give succinimide 27. Reduction with lithium aluminum hydride gives the pyrrolidino compound 28.

Scheme 4 describes the preparation of the analogous 6,7-methylenedioxy compounds. 3,4-Methylenedixoybenzonitrile is reduced with borane to give the phenylethylamine 29. This compound is treated by the procedures described in Scheme 3 for compounds 26 and 28 to give the corresponding phenylpyrrolinio (33) and phenylethyl (35) compounds.

Scheme 5 describes the preparation of chiral tetrahydroisoquinolines. The racemic intermediate 24 is reacted with chiral phenylglycinol in an inert solvent such as tetrahydrofuran with coupling reagents (for example, 1-(3-dimethylaminopropyl-3-ethylcarbodiimide hydrochloride and 1-hydroxybenzotriazole) to give the two stereoisomers which are separable by chromatography. Reduction with a reducing agent such as aluminum hydride gives N-methyl compounds 37 and 39. Catalytic hydrogenation gives chiral amines 38 and 40.

Scheme 6 shows the elaboration of the chiral phenyl pyrrolidinyl side chain. The chiral phenyl succinic acids are reduced with diborane to give the chiral butanediols 41 and 43. These alcohols are then activated, for example with mesyl chloride, to give the mesylates 42 and 44. These mesylates are then reacted with intermediates 38 and 40 to give chiral phenylpyrrolino tetrahydroisoquinolines 45, 46, 47 and 48.

Scheme 7 illustrates the preparation of the N-methyl-N-phenylethylaminomethyl side chain chiral tetrahydroisoquinolines. Compounds 38 and 40 are reacted with phenylacetic acid to give amides 49 and 52. Reduction (for example, diborane) in an inert solvent (for example, THF) gives the phenylethyl compounds 50 and 53. Formylation under reducing conditions (formaldehyde and sodium cyanoborohydride) gives tertiary amines 51 and 54.

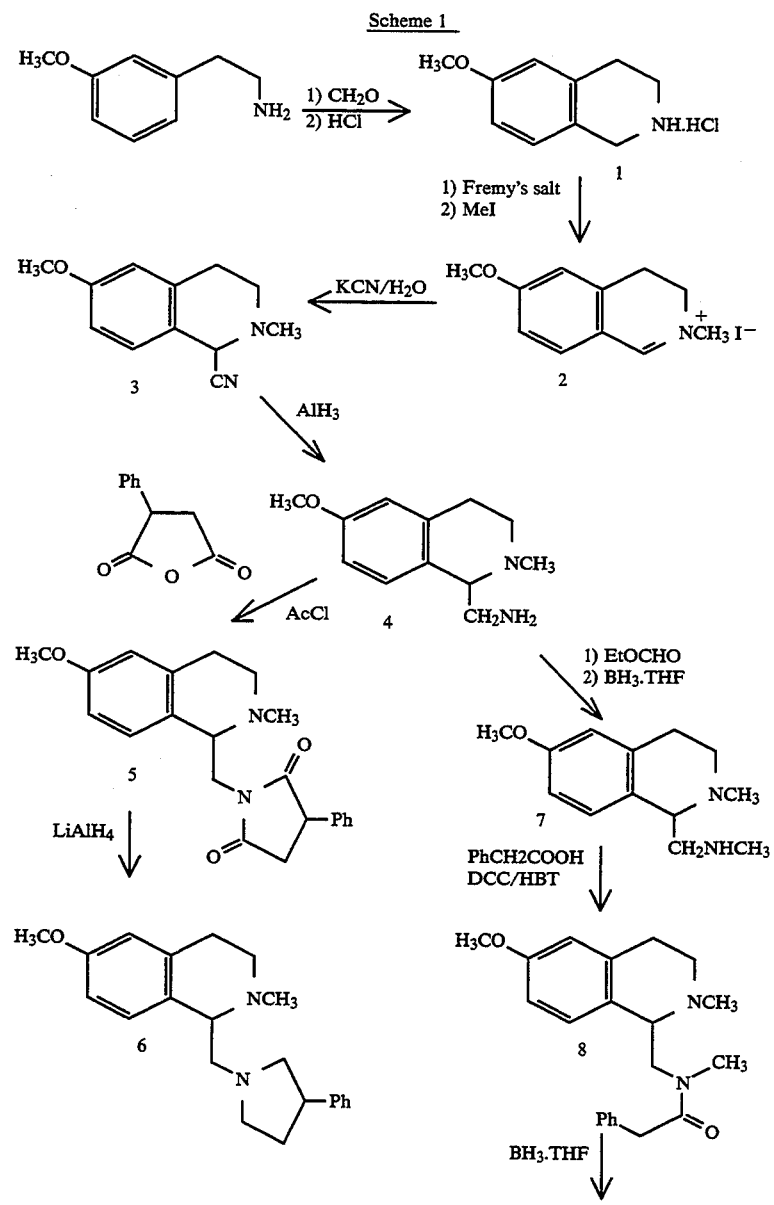

Scheme 1

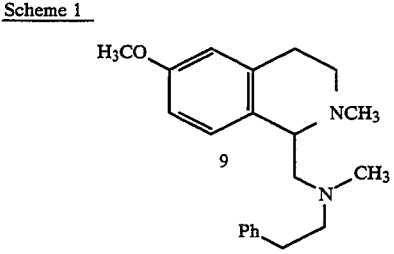
Scheme 1
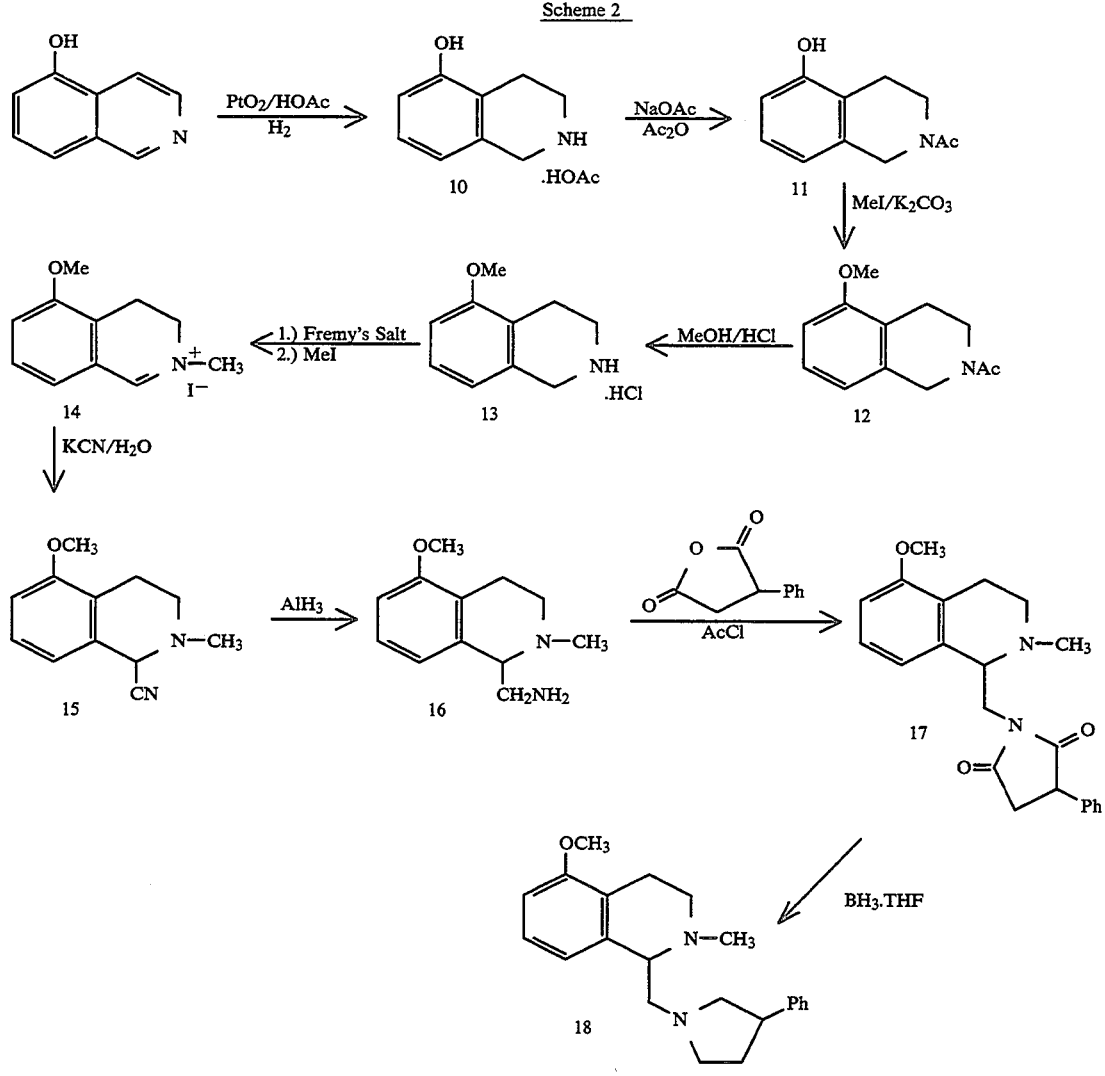
Scheme 2
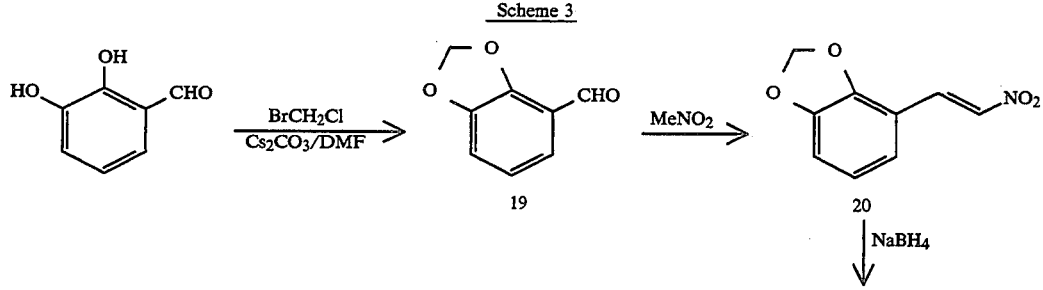
Scheme 3

-continued
Scheme 3
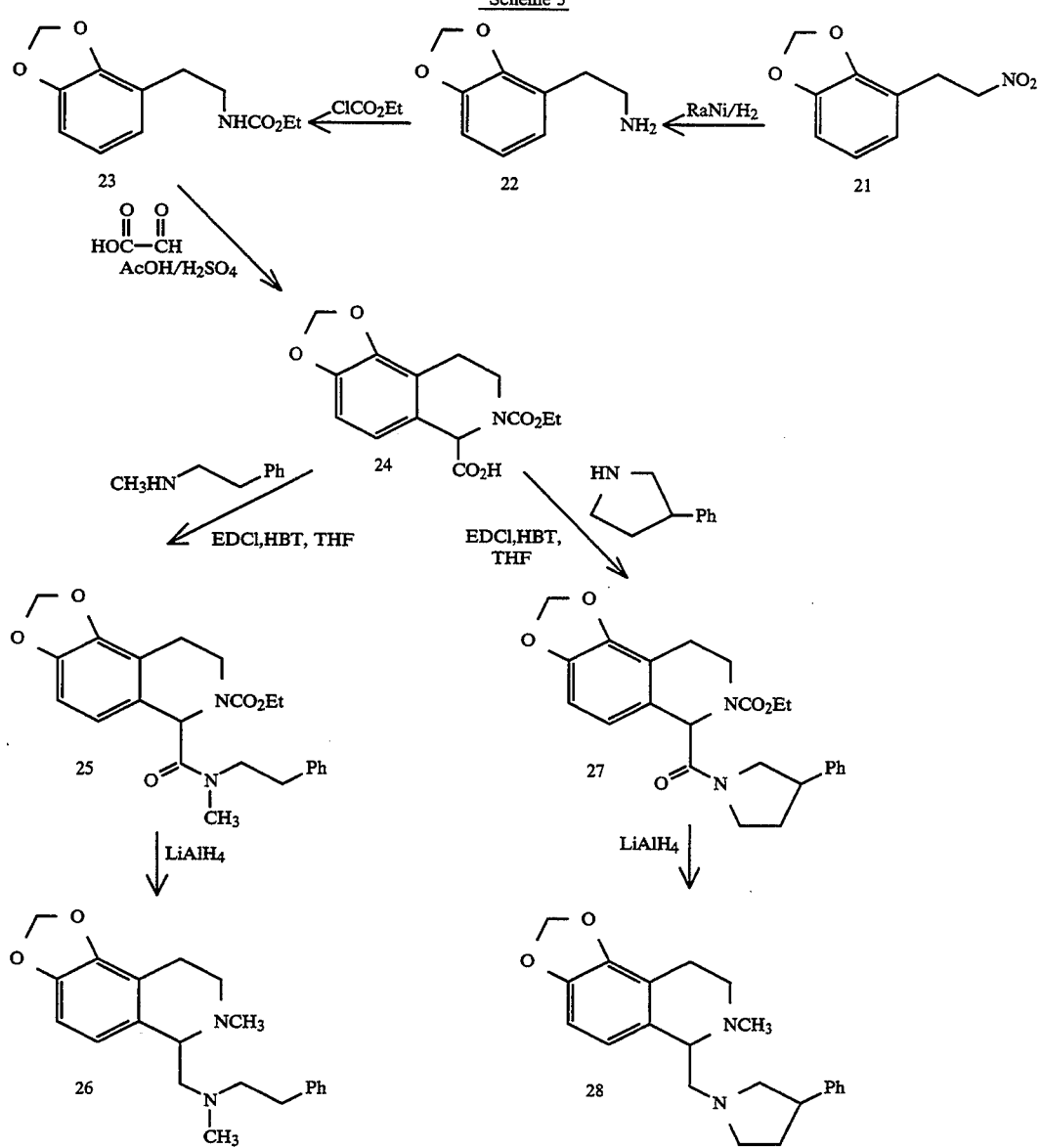
Scheme 4
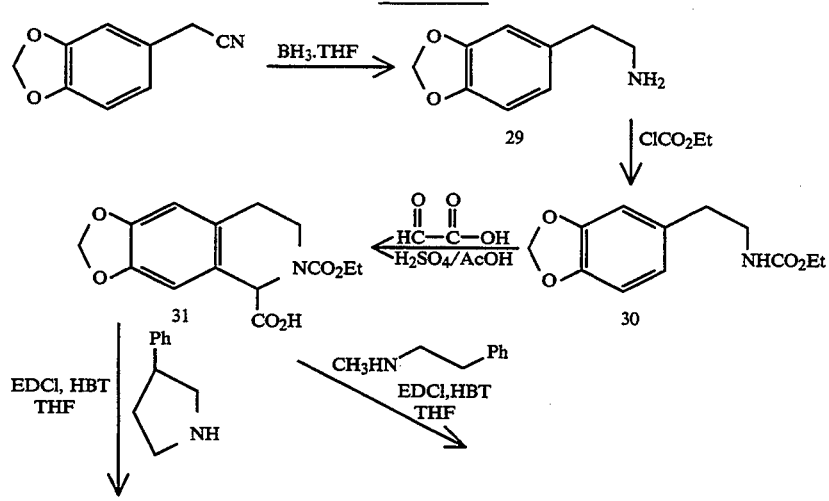

-continued
Scheme 4
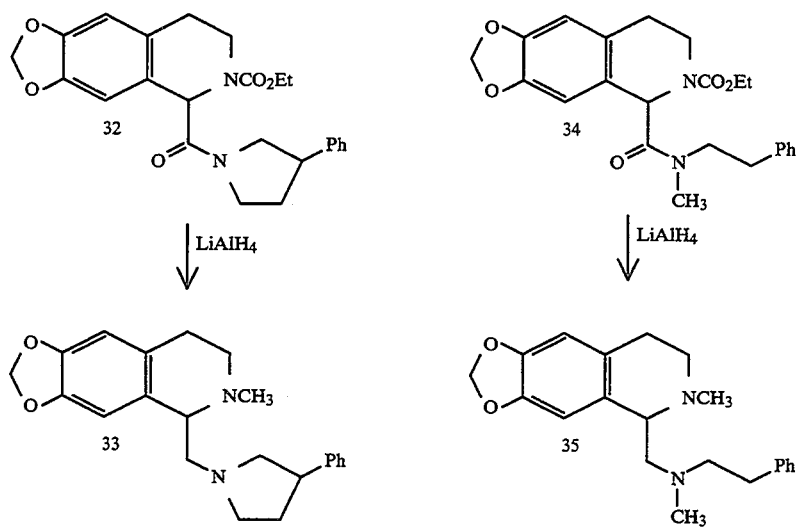
Scheme 5
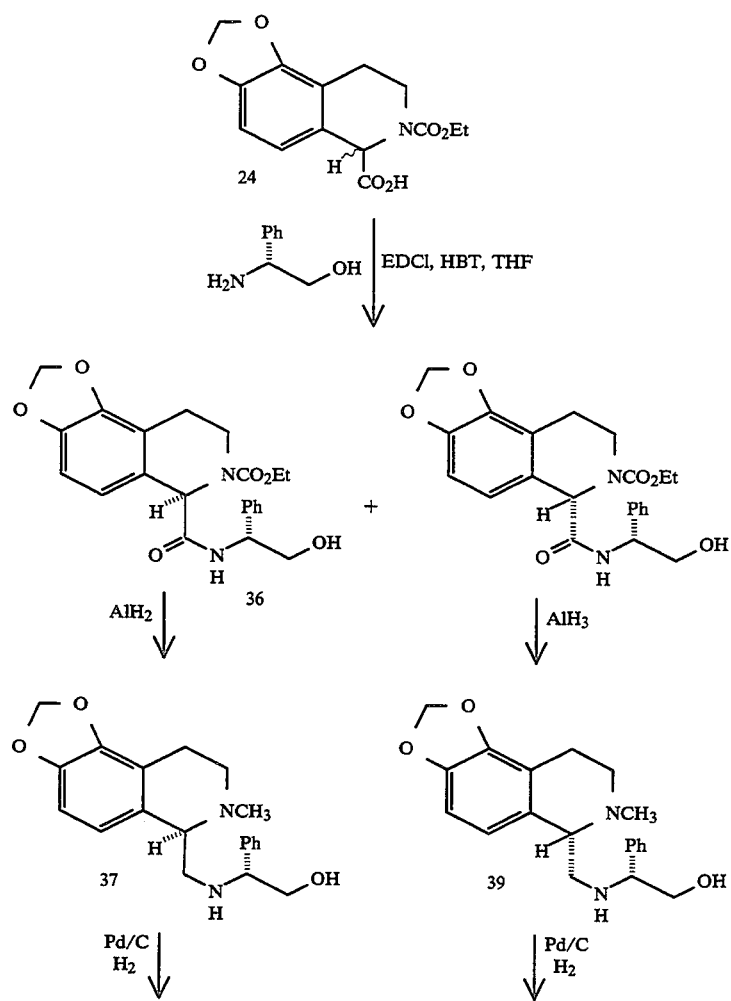

-continued
Scheme 5
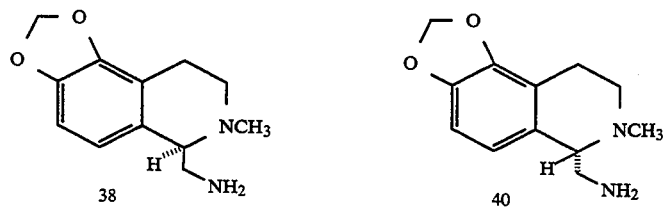
Scheme 6
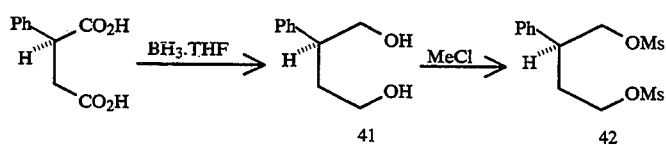
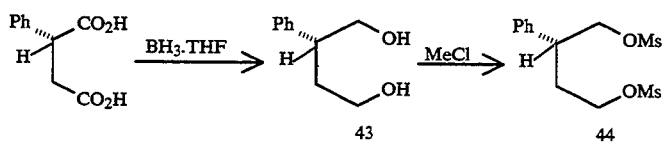
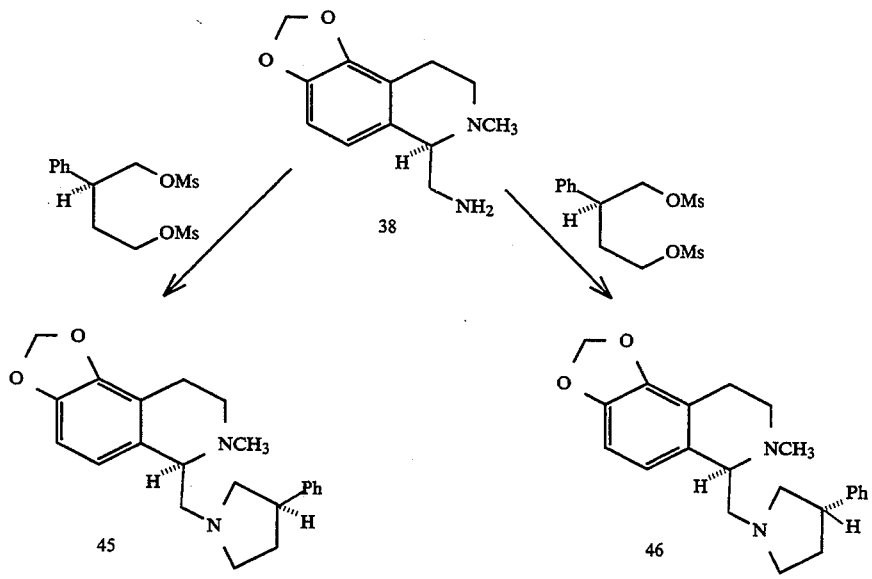
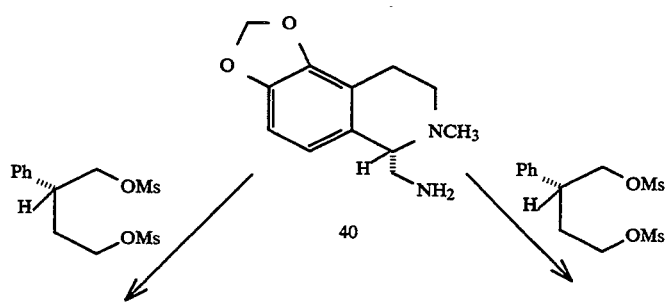

Scheme 6

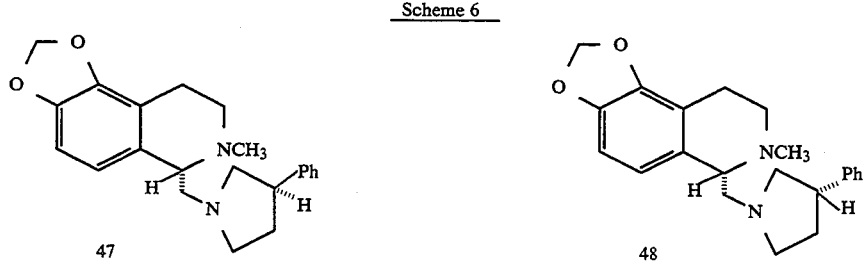

Scheme 7

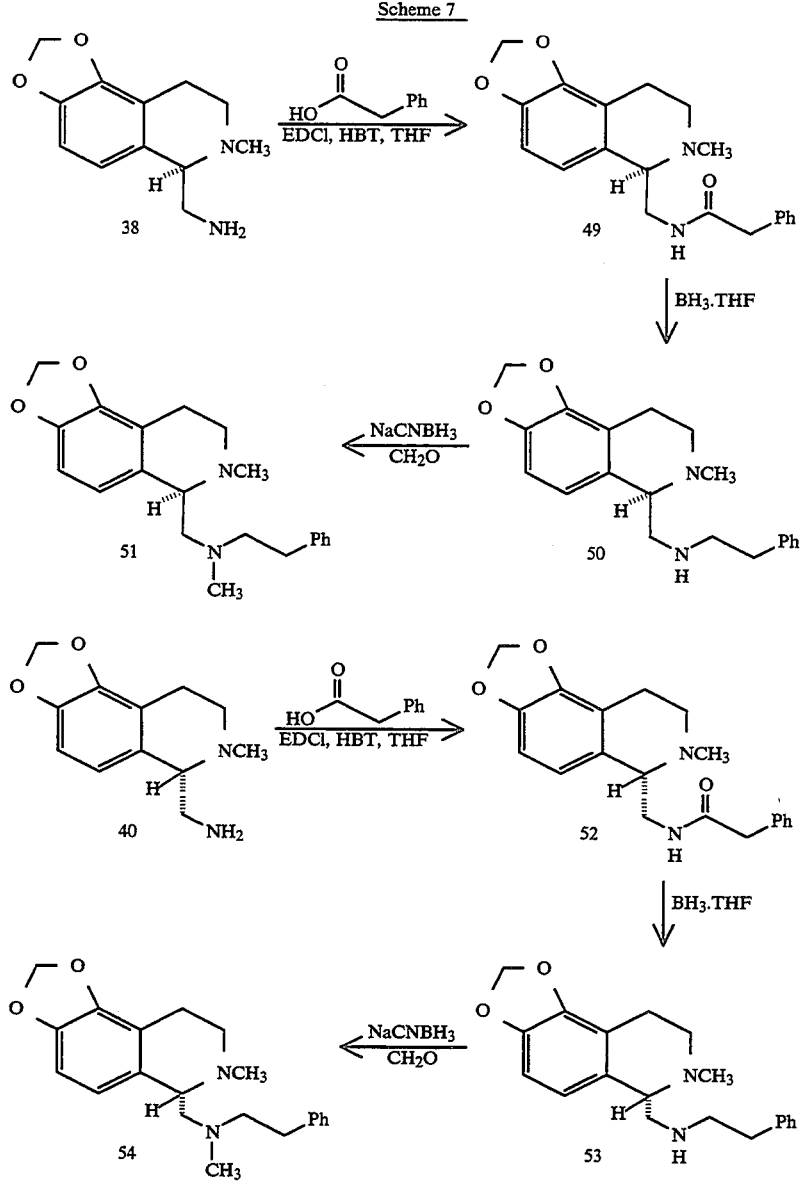

The following examples are merely illustrative of the invention and are not to be viewed as limiting the scope of the invention as it is defined by the appended claims. In the examples the abbreviations and MeOH stand for triethylamine and methanol, respectively.

EXAMPLE 1

6-Methoxy-2-methyl-1-(3,phenylpyrrolidino)methyl-1,2,3,4-tetrahydroisoquinoline

Step A—Preparation of 6-Methoxy-1,2,3,4-tetrahydroisoquinoline hydrochloride

37% Formalin was added to 3-methoxyphenylethylamine (23.3 g, 0.15 mol) with stirring at room temperature, followed by 12 mL of water. The mixture was stirred for 20 minutes at room temperature then heated at 100° C. for 1 hour. After cooling to room temperature, the mixture was extracted with toluene. The combined extracts were washed with brine, dried (MgSO$_4$), filtered, and evaporated under reduced pressure to obtain a yellow oil. The oil was heated at 100° C. with 33 mL 6N HCl for 2 hours. After cooling to room temperature, the solution was basified with 20% NaOH. The mixture was extracted with methylene chloride. The combined extracts were washed with H$_2$O and brine, dried (MgSO$_4$), filtered, and evaporated under reduced pressure to afford an oil which was converted to its hydrochloride salt as a white solid (23.5 g, 79% ). m.p. 230°–232° C.

Step B—Preparation of 6-Methoxy-2-methyl-3,4-dihydroisoquinolinonium iodide

The product resulting from Step A (5.0 g, 25.1 mmol) was added to a solution of Fremy's Salt (14.0 g, 54 mmol), sodium carbonate (45.7 g), and 900 mL of water. The reaction mixture was stirred at room temperature for 1.25 hours and then extracted with methylene chloride. The combined extracts were washed with H$_2$O and brine, dried (MgSO$_4$), filtered, and evaporated in vacuo to obtain 4.8 g yellow oil The crude dihydroisoquinoline was dissolved in 50 mL of methylene chloride, cooled to 0° C. with stirring, and 70 mL of methyl iodide was added. The reaction mixture was stirred at reflux for 0.5 hours, cooled to room temperature, and the solvents were evaporated under reduced pressure. The residue was crystallized from EtOH/ether to afford 4.08 g of the tire compound as a tan solid (54%).

Step C—1-Cyano-6-methoxy-2-methyl-1,2,3,4-tetrahydroisoquinoline

To the product resulting from Step B (4.08 g, 13.5 mmol) dissolved in 30 mL of warm water and stirred vigouously was added a solution of KCN (1.13 g, 17.4 mmol) in 23 mL of water dropwise. The reaction mixture was stirred at room temperature for 0.75 hour then was extracted with ethyl acetate. The combined extracts were washed with water and brine, dried (MgSO$_4$), filtered and evaporated in vacuo to afford 2.3 g of the title compound as a yellow oil (85%).

Step D—Preparation of 1-Aminomethyl-6-methoxy-2-methyl-1,2,3,4-tetrahydroisoquinoline Aluminum hydride was prepared by adding 1.8 mL of 100% H$_2$SO$_4$ dropwise to a solution of 130 mL of 0.5M LiAlH$_4$ in ether under N$_2$. External cooling was applied during the addition. The reaction mixture was stirred mechanically for 2 hours at room temperature, then allowed to stand at room temperature for 2 hours. The resultant thick, white solid was removed by filtration under a flow of N$_2$ and was cautiously destroyed by adding 1:1 H$_2$O-THF.

The ether filtrate from above was stirred at room temperature under N$_2$ as a solution of the product resulting from Example 1C(2.3 g, 11.4 mmol)and 50 mL 1:1 ether-THF was added dropwise. The reaction mixture was stirred at room temperature for 18 hours. The reaction mixture was cooled to 0° C. and 25 mL 1:1 H$_2$O-THF was added dropwise. THF was removed in vacuo and the residue was dissolved in ethyl acetate. The solution was washed with H$_2$O and brine, dried (MgSO$_4$) filtered and evaporated under reduced pressure to obtain 1.7 g of the title compound as an orange oil (72%).

Step E—Preparation of 6-Methoxy-2-methyl-1-(3-phenylsuccinimido)methyl-1,2,3,4-tetrahydroisoquinoline A solution of phenylsuccinic acid (20.0 g, 0.10 mol), acetyl chloride, and 200 mL of toluene was stirred at reflux for 5.5 hours, removing H$_2$O azeotropically during the reaction. After cooling to room temperature, toluene was evaporated in vacuo, and the residue was crystallized from ether to obtain 12.2 g of phenyl succinic anhydride as a white solid.

A solution of the product resulting from Step D (1.69 g, 7.6 mmol), phenylsuccinic anhydride from above (1.47 g, 8.4 mmol), and 20 mL 1,2-dichloroethane was stirred at room temperature for 1.0 hour. Acetyl chloride (1.08 mL, 15.2 mmol) was added and the reaction mixture was stirred at reflux for 1.5 hours and for 18 hours at room temperature. Saturated aqueous sodium bicarbonate was added and the solution was extracted with methylene chloride. The combined organic extracts were washed with brine, dried (MgSO$_4$), filtered, and evaporated in vacuo to yield 3.0 g of the title compound as a yellow oil.

Step F—Preparation of 6-Methoxy-2-methyl-1-(3-phenylpyrrolidino)methyl-1,2,3,4-tetrahydroisoquinoline dihydrochloride A solution of the product resulting from Step E (1.8 g, 4.9 mmol) and 18 mL anhydrous THF was added to a 1.0M solution of LiAlH$_4$ in THF (12.6 mL) at room temperature under N$_2$. The reaction mixture was stirred at reflux for 2.5 hours. After cooling to 0° C., the following sequence was added: 0.48 mL of H$_2$O, 0.48 mL of 15% KOH followed by 1.4 mL of H$_2$O. The mixture was stirred at room temperature for 1 hour, filtered through Celite ®, and evaporated under reduced pressure to obtain 1.52 g of an orange oil. The product was purified by column chromatography on silica gel eluting with 7:3 hexane-ether saturated with NH$_4$OH to obtain the desired product. Conversion to the dihydrochloride salt and crystallization from EtOH/ether afforded 0.31 g of the title compound as a white solid. m.p. 240°–241° C. Anal calc for C$_{22}$H$_{30}$Cl$_2$N$_2$O: C, 64.54; H, 7.39; N, 6.84. Found: C, 64.19; H, 7.43; N, 6.67.

EXAMPLE 2

6-Methoxy-2-methyl-1-((N-methyl-N-(2-phenylethyl)amino)methyl)-1,2,3,4-tetrahydroisoquinoline dihydrochloride Step A—Preparation of 6-Methoxy-2-methyl-1-(N-methylamino)methyl-1,2,3,4-tetrahydroisoquinoline Ethyl formate (2.9 mL) was added to a solution of the product resulting from Example 1D (1.8 g, 8.7 mmol) and 29 mL of toluene. The reaction mixture was stirred at reflux for 1.5 hours and then cooled to room temperature. Solvents were evaporated under reduced pressure and the residue was stirred at room temperature with 60 mL of anhydrous THF as 1.0M BH$_3$.THF (13.0 mL) was added dropwise. The reaction mixture was stirred at reflux for 2.5 hours. and for 18 hours at room temperature. After cooling to 0° C., methanolic HCl was added slowly. Solvents were evaporated in vacuo and the residue was converted to the free base to obtain 1.6 g of the title compound as an oil (87%).

Step B—Preparation of 6-Methoxy-2-methyl-1-(((N-methyl-N-phenylacetyl)amino)-methyl)-1,2,3,4-tetrahydroisoquinoline A solution of the product resulting from Example 2A (1.6 g, 7.5 mmol), 1,3-dicyclohexylcarbodiimide (1.7 g, 8.3 mmol), 1-hydroxybenzotriazole hydrate (2.2 g, 16.6 mmol), phenylacetic acid (1.0 g, 7.5 mmol) and 38 mL of THF was stirred at room temperature for 18 hours. The solid was filtered and the THF evaporated under reduced pressure. The residue was dissolved in methylene chloride, washed with 1N KOH, H$_2$O and brine, dried (MgSO$_4$), filtered and evaporated in vacuo to afford 2.4 g of crude product as an oil. Purification by preparative high pressure liquid chromatography, normal phase, eluting with 1,2-dichloroethane containing 5% MeOH afforded 1.5 g of the title compound as an oil (59%).

Step C—Preparation of 6-Methoxy-2-methyl-1-((N-methyl-N-(2-phenylethyl)amino)methyl)-1,2,3,4-tetrahydroisoquinoline dihydrochloride A solution of the product resulting from Example 2B (1.5 g, 4.4 mmol), 15 mL of anhydrous THF, and 11.1 mL of 1.0 molar BH$_3$.THF was stirred at reflux for 2.5 hours. After cooling to 0° C., methanolic HCl was added. The solution was stirred at reflux for 1 hour. After cooling to room temperature, solvents were evaporated under reduced pressure. The residue was dissolved in methylene chloride, washed with 10% NH$_4$OH and brine, dried (MgSO$_4$), filtered, and evaporated in vacuo to afford the desired product as the free base. Column chromatography on silica gel eluting with 1:1 hexane-ether saturated with NH$_4$OH afforded 0.37 g of pure free base. Conversion to the dihydrochloride salt and crystallization from EtOH/ether afforded the desired product (0.26 g). m.p. 108°–110° C. Anal calc for C$_{21}$H$_{30}$Cl$_2$N$_2$O: C, 63.47; H, 7.61; N, 7.05. Found: C, 63.20; H, 7.64; N, 6.97.

EXAMPLE 3

5-Methoxy-2-methyl-1-(3-phenylpyrrolidino)methyl-1,2,3,4-tetrahydroisoquinoline

Step A—Preparation of 5-Hydroxy-1,2,3,4-tetrahydroisoquinoline acetate

5-Hydroxyisoquinoline (9.0 g, 62 mmol) was dissolved in 150 mL of HOAc and hydrogenated at room temperature using 0.5 g of PtO$_2$ as a catalyst and 4 atmospheres pressure of H$_2$ for 18 hours. The solution was filtered, evaporated, and azeotroped with toluene several times to afford 12.1 g of the title compound as a gray solid (93%).

Step B—Preparation of 2-Acetyl-5-hydroxy-1,2,3,4-tetrahydroisoquinoline

Acetic anhydride (8.5 mL, 90 mmol) was added to a 0° C. solution of the product resulting from Step A (5.0 g, 24 mmol), NaOAc (3.9 g, 48 mmol, anhydrous) and 85 mL of MeOH. The reaction mixture was stirred for 0.5 hours at 0° C., then H$_2$O was added and the solvents were evaporated in vacuo. 1N HCl was added to the remaining slurry, and the resultant solid was filtered, washed with H$_2$O and dried in vacuo to afford 3.6 g of the title compound as a gray solid (77%).

Step C—Preparation of 2-Acetyl-5-methoxy-1,2,3,4-tetrahydroisoquinoline

The product resulting from Step B (6.0 g, 31.5 mmol) was stirred at reflux with K$_2$CO$_3$ (24.1 g, 117 mmol, powder), methyl iodide (5.3 mL, 85 mmol) and 620 mL of acetone for 3 hours. An additional 5.3 mL of methyl iodide was added and reflux was continued for another 6 hours. After cooling to room temperature, the mixture was filtered and the filtrate was evaporated in vacuo. The residue was dissolved in methylene chloride and washed with 1N KOH, 1N HCl, H$_2$O and brine. The solution was dried (MgSO$_4$), filtered and evaporated under reduced pressure to afford the title compound as an oil (5.9 g, 91%).

Step D—Preparation of 5-Methoxy-1,2,3,4-tetrahydroisoquinoline hydrochloride

A solution of the product resulting from Step C (5.9 g, 28.7 mmol), 59 mL MeOH and 24 mL concentrated HCl was stirred at reflux for 3 hours. After cooling to room temperature, the solvent was evaporated under reduced pressure and azeotroped with toluene. The resultant off white solid was recrystallized from MeOH/ether to afford 4.2 g of the title compound as a white solid (73%).

Step E—Preparation of 5-Methoxy-2-methyl-1-(3-phenylsuccinimido)methyl-1,2,3,4-tetrahydroisoquinoline Using the procedures described in Examples 1B, 1C, 1D and 1E, and the compound resulting from Example 3D, the title compound was prepared.

Step F—Preparation of 5-Methoxy-2-methyl-1-(3-phenylpyrrolidino)methyl-1,2,3,4-tetrahydroisoquinoline dihydrochloride BH$_3$.THF (1.0M solution, 8.1 mL) was added to a solution of the product resulting from Example 3E (0.98 g, 2.7 mmol) and 10 mL anhydrous THF. The reaction mixture was stirred at reflux for 1.0 hour and for 18 hours at room temperature. Methanolic HCl was added and the solution was stirred at reflux for 2 hours. Solvents were evaporated under reduced pressure and the residue was azeotroped with toluene. The crude product was purified by preparative HPLC, eluting with 18:1:1 EtOAc-H$_2$O -formic acid. The resultant formate salt was converted to its HCl salt and triturated with ether, faltered, and dried in vacuo to afford 0.40 g of the title compound as a white solid. m.p. 152°–153° C. Anal calc for C$_{22}$H$_{30}$Cl$_2$N$_2$O. 0.5 H$_2$O: C, 63.15; H, 7.47; N, 6.70. Found: C, 62.93; H, 7.39; N, 6.37.

EXAMPLE 4

5,6-Methylenedioxy-2-methyl-1-((N-methyl-N-(2-phenylethyl)amino)methyl)-1,2,3,4-tetrahydroisoquinoline dihydrochloride.

Step A—Preparation of 2,3-Methylenedioxybenzaldehyde

Starting with 2,3-dihydroxybenzaldehyde and using the procedure described in Tetrahedron Letters 32(22): 2461 (1991) afforded the title compound.

Step B—Preparation of 2,3-Methylenedioxy-b-nitrostyrene

The product resulting from Step A was stirred at reflux with 7.2 g NH$_4$OAc, nitromethane (12.7 mL, 0.24 mol) and 120 mL of glacial acetic acid for 1.5 hours. The mixture was cooled to room temperature and poured onto a mixture of ice and concentated HCl with stirring. The solid was faltered, washed with water and dried in vacuo to afford an orange solid. The crude product was purified by column chromatography eluting with 9:1 hexane-ethyl acetate to afford 13.9 g of the title compound as a yellow solid (65%).

Step C—Preparation of 1-Nitro-2-(2,3-methylenedioxyphenyl)ethane

The products resulting from Step B (3.18 g, 16.5 mmol) was dissolved in 27 mL of dioxane and added slowly over 0.5 hours to a suspension of NaBH$_4$ (1.37 g, 35 mmol), 8.6 mL of EtOH and 27 mL of dioxane. The internal temperature was kept below 30° C. The reaction mixture was stirred for 0.75 hours at room temperature, then ice was added cautiously, followed by a slow addition of 15 mL of 50% HOAc. The mixture was stirred for 0.5 hours at room temperature, then EtOH was removed in vacuo and methylene chloride added. The methylene chloride layer was washed three times with water and brine, dried (MgSO$_4$), filtered and evaporated under reduced pressure to afford 3.2 g of the title compound as a yellow oil (100%).

Step D—Preparation of 2,3-Methylenedioxyphenylethylamine

The product resulting from Step C (8.4 g, 43.0 mmol) was hydrogenated with a Raney nickel catalyst (10.3 g) in 250 mL of MeOH at room temperature under 4 atmospheres of H$_2$ for 18 hours. The solution was filtered and evaporated in vacuo to afford an oil which was convened to its hydrochloride salt and crystallized from EtOH/ether to afford 5.0 g of the title compound as a white solid (71%).

Step E—Preparation of 2-(2,3-Methylenedioxyphenyl)-N-(carboxyethyl)ethylamine

To a 0° C. solution of the product resulting from Step D (4.7 g, 28.4 mmol), triethylamine (4.4 mL, 31.3 mmol) and 78 mL of methylene chloride was added ethyl chloroformate (3.1 mL, 31.3 mmol). The reaction mixture was stirred at 0° C. for 1 hour and then ice/H$_2$O was added, and the layers were separated. The organic phase was washed with 1N KOH, 1N HCl, H$_2$O and brine, dried (MgSO$_4$), filtered, and evaporated under reduced pressure to afford an oil which was purified by column chromatography eluting with 7:3 hexane-ethyl acetate to afford 6.0 g of the title compound as a clear oil (89%).

Step F—Preparation of 2-Aza-2-(carboxyethyl-5,6-methylenedioxy)-1,2,3,4-tetrahydro-1-naphthoic acid The product resulting from Step E (6.0 g, 25.3 mmol) was stirred at 0° C. in 51 mL 3:1 AcOH-H$_2$SO$_4$ as glyoxylic acid monohydrate (2.1 g, 22.8 mmol) was added. The reaction mixture was stirred at 0° C. for 0.25 hours and at room temperature for 18 hours. Ice/H$_2$O was added, and the mixture was extracted with ethyl acetate. The combined organic extracts were washed 3 times with water and brine, dried (MgSO$_4$), filtered and evaporated to afford a tan foam. The crude product was purified by column chromatography eluting with 7:3 hexane-ethyl acetate containing 1% HOAc to afford 5.3 g of the title compound as a white foam (72%).

Step G—Preparation of 2-Aza-2-(carboxyethyl-5,6-methylenedioxy)-1,2,3,4tetrahydro-1-naphthoyl-N-methyl phenylethylamine A mixture of the product resulting from Step F (1.1 g, 3.9 mmol), N-methylphenylethylamine (0.56 mL, 3.9 mmol), 1-(3-dimethylaminopropyl)-3-ethylcarbodiimide hydrochloride, 1-hydroxybenzotriazole hydrate (1.2 g, 9.0 mmol), Et$_3$N (0.63 mL, 4.5 mmol), and 10.0 mL of THF was stirred at room temperature for 1.5 hours. H$_2$O was added and the mixture was extracted with ethyl acetate. The combined organic extracts were washed with 1N KOH, 1N HCl, H$_2$O and brine, dried (MgSO$_4$), filtered and evaporated in vacuo to afford 1.4 g of the title compound as an orange oil (89%).

Step H—Preparation of 5,6-Methylenedioxy-2-methyl-1 ((N-methyl-N-(2phenylethyl)amino)Methyl-1,2,3,4-tetrahydroisoquinoline dihydrochloride To the product resulting from Step G (1.4 g, 3.4 mmol) dissolved in 15 mL of THF and stirred at room temperature was added 1.0 M LiAlH$_4$ in THF (8.9 mL). The reaction mixture was stirred at reflux for 2.5 hours. After cooling to 0° C., the following sequence was added: 0.34 mL of H$_2$O, 0.34 mL of 15% KOH and 1.0 mL of H$_2$O. After stirring 1 hour at room temperature, the mixture was filtered through Celite ®, and the filtrate evaporated to afford 0.97 g of an orange oil. The crude product was purified by column chromatography eluting with 8:2 hexane-ether saturated with NH$_4$OH. The pure free base was converted to its dihydrochloride salt and dried in vacuo to afford 0.82 g of the title compound as a white solid (59%). m.p. 161°–162° C. Anal calc for C$_{21}$H$_{28}$Cl$_2$N$_2$O$_2$. H$_2$O: C, 58.74; H, 7.04; N, 6.52. Found: C, 58.67; H, 6.76; N, 6.49.

EXAMPLE 5

5,6-Methylenedioxy-2-methyl-1-N-(3-phenylpyrrolinodino)methyl-1,2,3,4-tetrahydroisoquinoline dihydrochloride Using the procedures described in Example 4 and substituting 3-phenylpyrrolidine for N-methylphenylethylamine in Example 4, Step G provided the desired product. m.p. 248°–250° C. Anal calc for C$_{22}$H$_{28}$Cl$_2$N$_2$O$_2$. 641 1.5 H$_2$O: C, 58.67; H, 6.94; N, 6.22. Found: C, 59.03; H, 6.73; N, 6.00.

EXAMPLE 6

6,7-Methylenedioxy-2-methyl-1-(3-phenylpyrrolidino)-methyl-1,2,3,4-tetrahydroisoquinoline dimethanesulfonate Step A—Preparation of 3,4-Methylenedioxyphenylethylamine To a solution of 3,4-methylenedioxyphenyl-acetonitrile (3.22 g, 20 mmol) dissolved in 40 mL anhydrous THF was added 1.0M BH$_3$.THF (30 mL). The reaction mixture was stirred at room temperature for 0.5 hours and then at reflux for 3.5 hours. After cooling to 0° C., 20 mL MeOH was added dropwise followed by 10 mL of isopropyl alcohol saturated with HCl gas. The solution was stirred at reflux for 0.5 hours, cooled to room temperature and concentrated to about 25 mL under reduced pressure. H$_2$O was added and the mixture was washed with ether. The aqueous layer was basified with 1N KOH and washed with methylene chloride. The methylene chloride extracts were washed with brine, dried (MgSO$_4$), filtered and evaporated in vacuo to afford 2.4 g of the title compound as a clear oil (73%).

Step B—Preparation of 6,7-Methylenedioxy-2-methyl-1-(3-phenylpyrrolidino)methyl-1,2,3,4-tetrahydroisoquinoline dimethanesulfonate Using the procedures described in Example 5 and the compound resulting from Example 6, Step A provided the desired product. The free base obtained from the LiAlH$_4$ reduction was converted to its dimethanesulfonate salt. m.p. 193°–194° C. Anal calc for C$_{24}$H$_{34}$N$_2$S$_2$O$_8$. H$_2$O: C, 51.41; H, 6.13; N, 5.01. Found: C, 51.94; H, 6.13; N, 5.01.

EXAMPLE 7

6,7-Methylenedioxy-2-methyl-1-((N-methyl-N-(2-phenylethyl)amino)methyl)-1,2,3,4-tetrahydroisoquinoline dihydrochloride Using the compound resulting from Example 6, Step A and the procedures described in Example 2 the title compound was prepared. m.p. 165°–166° C. Anal calc for C$_{21}$H$_{28}$Cl$_2$N$_2$O$_2$. 0.5 H$_2$O: C, 60.00; H, 6.95; N, 6.66. Found: C, 59,55; H, 6.58; N, 6.57.

EXAMPLE 8

5,6-Methylenedioxy-2-methyl-1(R)-(3'(R)-phenylpyrrolidino)methyl-1,2,3,4-tetrahydroisoquinoline dihydrochloride Step A—Preparation of 2-Aza-2-carboxyethyl-5,6-methylenedioxy-1,2,3,4-tetrahydro-1(R)- and 1(S)-naphthoyl-2-hydroxy-1(R)-phenylethylamine Using the procedure outlined for Example 4, Step G, but substituting (R)-phenylglycinol for N-methylphenylethyl amine provided a mixture of the 1-(R) and the 1(S) amides. These products were separated by preparative HPLC, eluting with 2:1 ethyl acetate-methylene chloride.

Step B—Preparation of 5,6-Methylenedioxy-2-methyl-1(R)-[(2-hydroxy-1(R)phenylethyl)aminomethyl]-1,2,3,4-tetrahydroisoquinoline dihydrochloride Using the procedure outlined for Example 1, Step D, but substituting the 1-(R)-amide obtained from Example 8A for Example 1, Step C, provided the desired product. The product was converted to its dihydrochlorde salt using ethanol/ethereal HCl.

Step C—Preparation of 1(R)-Aminomethyl-5,6-methylenedioxy-2-methyl-1,2,3,4-tetrahydroisoquinoline A mixture of the product resulting from Step B (1.8 g, 4.0 mmole), a catalytic amount of 10% Pd/C (dry) and 150 mL of MeOH was hydrogenated at 4 atmospheres of $H_2$ at room temperature overnight. The reaction mixture was filtered, the solvent evaporated under reduced pressure and the residue recrystallized from MeOH-ether to afford 0.8 g white solid. $[a]_D^{20°} = +25.5°$ (c=0.84, MeOH).

Step D—Preparation of 2(R)-Phenyl-1,4-butanediol

Using the procedure outlined for Example 9, Step A, but substituting R-(+)-phenylsuccinic acid (Fluka Chemical Co.) for S-(−)-phenylsuccinic acid afforded the desired product.

Step E—Preparation of 2(R)-Phenyl-1,4-butanediol bismesylate

Using the procedure outlined for Example 9, Step B, but substituting the compound resulting from Example 8D for Example 9A, provided the desired compound. $[a]_D^{20°} = -32.1°$ (c=1.01, MeOH).

Step F—Preparation of 5,6-Methylenedioxy-2-methyl-1(R)-(3'(R)-phenylpyrrolidino)methyl-1,2,3,4-tetrahydroisoquinoline dihydrochloride A solution of the compound resulting from Step C (0.15 g, free base, 0.68 mmol), the compound resulting from Example 8E (0.26 g, 1.0 mmol), 0.34 mL diisopropylethylamine and 1.6 mL absolute ethanol was stirred at reflux for 8 hours. Solvents were removed in vacuo, and the residue was purified by column chromatography on silica gel eluting with 7:3 hexane-ethyl acetate saturated with $NH_4OH$ to afford 0.11 g of the free base as a clear oil. The product was converted to the dihydrochloride (ethanol-ethereal HCl) to afford 0.15 g of the title compound as a white solid. m.p. 273°–274° C. $[a]_D^{20°} = +69.4°$ (c=0.51, $H_2O$). Anal calc for $C_{22}H_{28}Cl_2N_2O_2$. 0.5 $H_2O$: C, 61.11; H, 6.76; N, 6.48. Found: C, 61.20; H, 6.66; N, 6.23.

EXAMPLE 9

5,6-Methylenedioxy-2-methyl-1(R)-[3'(S)-phenylpyrrolidino]methyl-1,2,3,4-tetrahydroisoquinoline dihyrochloride Step A—Preparation of 2(S)-Phenyl-1,4-butanediol 1.0M $BH_3$·THF (51.5 mL) was added dropwise to a 0° C. solution of (S)-(+)-phenylsuccinic acid (5.0 g, 25.8 mmol, Fluka Chemical Co.) and 76 mL of anhydrous THF. The reaction mixture was stirred at 0° C. for 30 minutes and at room temperature for 2 hours. 30 mL of MeOH was added slowly and solvents were removed in vacuo. The residue was dissolved in methylene chloride and washed with 0.1N HCl dried ($MgSO_4$), filtered and evaporated under reduced pressure to afford 3.6 g of the title compound as a clear oil.

Step B—Preparation of 2(S)-Phenyl-1,4-butanediol bismesylate

Methanesulfonyl chloride (3.9 mL, 50.4 mmol) was added dropwise to a 0° C. solution of the product resulting from Step A (3.6 g, 21.7 mmol), triethylamine (8.6 mL) and 67 mL of methylene chloride. The reaction mixture was stirred for 2.5 hours at 0° C., then was diluted with methylene chloide, washed with saturated aqueous sodium bicarbonate, 0.5N HCl, dried ($MgSO_4$), filtered and evaporated under reduced pressure to afford 6.5 g as a solid. The product was puttied by column chromatography on silica gel eluting with 1:1 hexane-ethyl acetate to obtain 6.0 g of the title compound as a white solid. $[a]_D^{20°} = +33.5°$ (c=1.06, MeOH).

Step C—Preparation of 5,6-Methylenedioxy-2-methyl-1(R)-(3'(S)-phenylpyrrolidino)methyl-1,2,3,4-tetrahydroisoquinoline dihyrochloride Using the procedure outlined for Example 8, Step F, but substituting the compound resulting from Example 9B for Example 8E provided the desired product. m.p. 219°–220° C. Anal calc for $C_{22}H_{28}Cl_2N_2O_2$: C, 62.41; H, 6.67; N, 6.62. Found: C, 62.17; H, 6.75; N, 6.46. $[a]_D^{20°} = +36.2°$ (c=0.60, $H_2O$).

EXAMPLE 10

5,6-Methylenedioxy-2-methyl-1(S)-[3'(R)-phenylpyrrolidino]methyl-1,2,3,4-tetrahydroisoquinoline dihydrochloride Step A—Preparation of 5,6-Methylenedioxy-2-methyl-1(S)-((2-hydroxy-1(R)-phenylethyl)aminomethyl)-1,2,3,4-tetrahydroisoquinoline dihydrochloride Using the procedure outlined for Example 1, Step D, but substituting the 1-(S)-amide obtained from Example 8, Step A for Example 1, Step C, provided the desired product. The product was converted to the dihydrochloride using ethanolethereal HCl.

Step B—Preparation of 1(S)-Aminomethyl-5,6-methylenedioxy-2-methyl-1,2,3,4-tetrahydroisoquinoline Using the procedure outlined for Example 8, Step C, but substituting the compound resulting from Example 10, Step A for Example 8, Step B provided the desired compound. $[a]_D^{20°} = -27.2°$ (c=0.67, $H_2O$).

Step C—Preparation of 5,6-Methylenedioxy-2-methyl-1(S)-[3'(R)-phenylpyrrolidino]methyl-1,2,3,4-tetrahyroisoquinoline dihydrochloride Using the procedure outlined for Example 8, Step F, but substituting the compound resulting from Example 10, Step B for Example 8, Step C provided the desired product. m.p. 149°–151° C. Anal calc for $C_{22}H_{28}Cl_2N_2O_2$: C, 62.41; H, 6.67; N, 6.62. Found: C, 62.87; H, 6.79; N, 6.51. $[a]_D^{20°} = -29.6°$ (c=0.62, $H_2O$).

EXAMPLE 11

5,6-Methylenedioxy-2-methyl-1(S)-[3'(S)-phenylpyrrolidino]methyl-1,2,3,4-tetrahydroisoquinoline dihydrochloride Using the procedure outined for Example 8, Step F, but substituting Example 10, Step B for Example 8, Step

EXAMPLE 12

5,6-Methylenedioxy-2-methyl-1(R)-(((N-methyl-N-phenylethyl)amino)methyl)-1,2,3,4-tetrahydroisoquinoline dihydrochloride Step A—Preparation of 5,6-Methylenedioxy-2-methyl-1(R)-(((N-phenylacetyl)amino)methyl-1,2,3,4-tetrahydroisoquinoline Using the procedure outlined for Example 4, Step G, but substituting phenylacetic acid for Example 4, Step F, and substituting the compound resulting from Example 8, Step C for N-methylphenylethyl amine afforded the desired product.

Step B—Preparation of 5,6-Methylenedioxy-2-methyl-1(R)-(((N-phenylethyl)amino)methyl)-1,2,3,4-tetrahydroisoquinoline Using the procedure outlined for Example 2, Step C, but substituting the compound resulting from Example 12, Step A for Example 2, Step B, provided the desired product as the free base.

Step C—Preparation of 5,6-Methylenedioxy-2-methyl-1(R)-(((N-methyl-N-phenylethyl)amino)methyl)-1,2,3,4-tetrahydroisoquinoline dihydrochloride Sodium cyanoborohydride (55 mg, 0.88 mmol) was added to a solution of the compound resulting from Step B (100 mg, 0.31 mmol), 1.0 mL 37% formaldehyde and 1.8 mL of MeOH. The reaction mixture was stirred at room temperature for 1 hour. Five drops of 6N HCl were added and the solvent evaporated under reduced pressure. 10 mL 10% NH$_4$OH was added to the residue and the solution was extracted with methylene chloride. The combined organic extracts were washed with brine, dried (MgSO$_4$), filtered and evaporated in vacuo to afford 90 mg of the title compound free base as an oil. The product was purified by column chromatography on silica gel eluting with 8:2 hexane-ethyl acetate saturated with NH$_4$OH. Conversion to the dihydrochloide (ethanol/ethereal HCl) afforded the desired product. m.p. 228°–229° C. Anal calc for $C_{21}H_{28}Cl_2N_2O_2$: C, 61.31; H, 6.86; N, 6.81. Found: C, 60.87; H, 6.89; N, 6.80. $[a]_D^{20°} = +25.5°$ (c=0.51, H$_2$O).

EXAMPLE 13

5,6-Methylenedioxy-2-methyl-1(S)-(((N-methyl-N-phenylethyl)amino)methyl-1,2,3,4-tetrahydroisoquinoline dihydrochloride Using the procedure outlined for Example 12, Step A, but substituting the compound resulting from Example 10, Step B for Example 8, Step C, provided 5,6-methylenedioxy-2-methyl-1-(S)-[(N-phenylacetyl)methylaminol-1,2,3,4-tetrahydroisoquinoline.

Using the procedure outlined for Example 2, Step C, but substituting the compound prepared above for Example 2, Step B provided 5,6-methylenedioxy-2-methyl-1(S)-(((N-phenylethyl)amino)methyl)-1,2,3,4-tetrahydroisoquinoline.

Using the procedure outlined for Example 12, Step C, but substituting the compound prepared above for Example 12, Step B, provided the title compound. m.p. 228°–229° C. Anal calc for $C_{21}H_{28}Cl_2N_2O_2 \cdot 0.5\ H_2O$: C, 60.00; H, 6.95; N, 6.66. Found: C, 60.33; H, 6.91; N, 6.58. $[a]_D^{20°} = -28.1°$ (c=0.75, H$_2$O).

The foregoing examples are provided as being illustrative of the invention and are not intended to limit the invention to the disclosed compounds. Variations and changes which are obvious to one skilled in the art are intended to be within the scope and nature of the invention which are defined in the appended claims.

We claim:

1. A compound of the formula

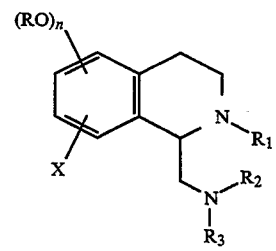

or a pharmaceutically acceptable salt thereof, wherein
n is an integer selected from the group consisting of 0 and 1,
R is independently selected from the group consisting of methyl and ethyl;
X is selected from the group consisting of hydrogen and fluorine;
R$_1$ is selected from the group consisting of
  alkyl of one to six carbon atoms,
  alkanoyl of from two to six carbon atoms,
  aminosulfonyl,
  alkoxycarbonyl of from two to eight carbon atoms, and
  aminocarbonyl;
R$_2$ is selected from methyl and ethyl; and
R$_3$ is arylalkyl where the aryl portion is unsubstituted or is substituted by one or more groups selected from the group consisting of
  alkyl of one to six carbon atoms,
  haloalkyl of one to six carbon atoms,
  alkoxy of one to six carbon atoms,
  thioalkoxy of one to six carbon atoms,
  amino,
  alkylamino of one to six carbon atoms,
  dialkylamino in which the alkyl groups are independently of one to six carbon atoms;
  hydroxy,
  halo,
  mercapto,
  nitro,
  carboxldehyde,
  carboxy,
  carboalkoxy of two to eight carbon atoms, and
  carboxamido; or
R$_2$ and R$_3$ taken together with the nitrogen atom to which they are attached form a pyrrolidinyl ring substituted by phenyl, which phenyl group is optionally substituted by one or more groups selected from the group consisting of
  alkyl of one to six carbon atoms,
  halo,
  hydroxy,
  alkoxy of one to six carbon atoms,
  amino, and
  thioalkoxy of one to six carbon atoms.

2. A compound as defined by claim 1 in which n is 1 and R$_1$ is methyl.

3. A compound as defined by claim 1 having the structure

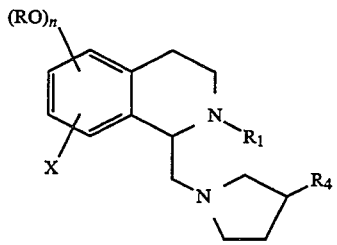

wherein $R_4$ is phenyl optionally substituted by one or more groups selected from the group consisting of
alkyl of one to six carbon atoms,
halo,
hydroxy,
alkoxy of one to six carbon atoms,
amino, and
thioalkyloxy of one to six carbon atoms.

4. A compound as defined by claim 1 having the structure

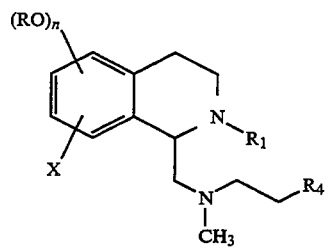

wherein $R_4$ is phenyl optionally substituted by one or more groups selected from the group consisting of
alkyl of one to six carbon atoms,
halo,
hydroxy,
alkoxy of one to six carbon atoms,
amino, and
thioalkyloxy of one to six carbon atoms.

5. A compound as defined by claim 3 wherein $R_1$ is methyl.

6. A compound as defined by claim 3 selected from the group consisting of:
6-methoxy-2-methyl-1-(3-phenylpyrrolidino)methyl-1,2,3,4-tetrahydroisoquinoline;
5-methoxy-2-methyl-1-(3-phenylpyrrolidino)methyl-1,2,3,4-tetrahydroisoquinoline;
5,6-methylenedioxy-2-methyl-1-(3-phenylpyrrolindino)methyl-1,2,3,4-tetrahydroisoquinoline;
6,7-methylenedioxy-2-methyl-1-(3-phenylpyrrolidino) methyl-1,2,3,4-tetrahydroisoquinoline;
5,6-methylenedioxy-2-methyl-1(R)-(3'(R)-phenylpyrrolidino)methyl-1,2,3,4-tetrahydroisoquinoline;
5,6-methylenedioxy-2-methyl-1(R)-(3'(S)-phenylpyrrolidino)methyl-1,2,3,4-tetrahydroisoquinoline;
5,6-methylenedioxy-2-methyl-1(S)-(3'R)-phenylpyrrolidino)methyl-1,2,3,4-tetrahyroisoquinoline; and
5,6-methylenedioxy-2-methyl-1(S)-(3'(S)-phenylpyrrolidino)methyl-1,2,3,4-tetrahydroisoquinoline.
or a pharmaceutically acceptable salt thereof.

7. A compound as defined by claim 4 selected from the group consisting of:
5,6-methylenedioxy-2-methyl-1-(N-methyl-N-(2-phenylethyl)amino)methyl)-1,2,3,4-tetrahydroisoquinoline;
6,7-methylenedioxy-2-methyl-1-((N-methyl-N-(2-phenylethyl)amino)methyl)-1,2,3,4-tetrahydroisoquinoline;
5,6-methylenedioxy-2-methyl-1(R)-(((N-methyl-N-phenylethyl)-amino)methyl-1,2,3,4-tetrahydroisoquinoline; and
5,6-methylenedioxy-2-methyl-1(S)-(((N-methyl-N-phenylethyl)-amino)methyl-1,2,3,4-tetrahydroisoquinoline.

8. A pharmaceutical composition comprising a therapeutically effective amount of a compound in accordance with claim 1 in combination with a pharmaceutically acceptable carrier.

9. A method for inhibiting biogenic amine uptake and antagonizing alpha-2 adrenoreceptors in a mammal in need of such treatment comprising administering to the mammal a therapeutically effective amount of a compound of claim 1.

10. A method of treating disorders which are mediated by biogenic amine uptake and antagonism of alpha-2 adrenoreceptors comprising administering to a mammal in need of such treatment a therapeutically effective amount of a compound as defined by claim 1.

* * * * *